United States Patent
Knopf

(10) Patent No.: US 11,633,204 B2
(45) Date of Patent: Apr. 25, 2023

(54) IRRIGATION FLUID FOR RESECTION

(71) Applicant: OLYMPUS WINTER & IBE GMBH, Hamburg (DE)

(72) Inventor: Christoph Knopf, Lübeck (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 486 days.

(21) Appl. No.: 16/775,572

(22) Filed: Jan. 29, 2020

(65) Prior Publication Data

US 2020/0246038 A1 Aug. 6, 2020

(30) Foreign Application Priority Data

Feb. 5, 2019 (DE) .................... 10 2019 102 839.6

(51) Int. Cl.
*A61B 17/32* (2006.01)

(52) U.S. Cl.
CPC ..... *A61B 17/320016* (2013.01); *A61B 2217/007* (2013.01); *A61B 2218/002* (2013.01)

(58) Field of Classification Search
CPC .......... A61B 2018/00029; A61B 2018/00196; A61B 2018/00601; A61B 2018/1407; A61B 2018/144; A61B 2018/1472; A61B 2018/1475; A61B 18/149; A61B 17/320016; A61B 2218/002; A61B 2217/007
See application file for complete search history.

(56) References Cited

U.S. PATENT DOCUMENTS

| | | | |
|---|---|---|---|
| 5,196,011 A | 3/1993 | Korth et al. | |
| 5,423,813 A * | 6/1995 | Kaiser | A61B 18/149 606/46 |
| 6,068,603 A | 5/2000 | Suzuki | |

(Continued)

FOREIGN PATENT DOCUMENTS

| | | |
|---|---|---|
| DE | 10122465 C1 | 8/2002 |
| DE | 102006053338 A1 | 5/2008 |

(Continued)

OTHER PUBLICATIONS

Dec. 8, 2021 Office Action issued in U.S. Appl. No. 16/811,675.
(Continued)

*Primary Examiner* — Linda C Dvorak
*Assistant Examiner* — Lindsay Regan Lancaster
(74) *Attorney, Agent, or Firm* — Oliff PLC

(57) ABSTRACT

An electrically conductive irrigation fluid for use in bipolar resectoscopic surgery, wherein the irrigation fluid being brought into contact with the electrode of a resectoscope and tissue being coagulated and/or resected by means of the electrode surrounded by the irrigation fluid, wherein the irrigation fluid includes metal ions. Moreover, the method relates to a resectoscopy system including a resectoscope and an irrigation system that is connected to the resectoscope, the resectoscope having a handle and a tubular shaft, and the shaft including an electrode instrument that is arranged so as to be longitudinally displaceable and has in its distal end region an electrode to which high-frequency current can be applied, wherein the irrigation system includes an irrigation fluid, which can be conducted through the shaft of the resectoscope to the electrode.

13 Claims, 1 Drawing Sheet

(56) References Cited

U.S. PATENT DOCUMENTS

| | | |
|---|---|---|
| 6,149,620 A | 11/2000 | Baker et al. |
| 7,150,745 B2 | 12/2006 | Stern et al. |
| 7,261,711 B2 | 8/2007 | Mulier et al. |
| 7,303,561 B2 | 12/2007 | Ouchi |
| 7,347,860 B2 | 3/2008 | Ouchi |
| 7,572,251 B1 | 8/2009 | Davison et al. |
| 7,815,639 B2 | 10/2010 | Brommersma |
| 9,072,443 B2 | 7/2015 | Hashido et al. |
| 2002/0111608 A1 | 8/2002 | Baerveldt et al. |
| 2002/0188293 A1 | 12/2002 | Manzo |
| 2002/0193792 A1 | 12/2002 | Valencic et al. |
| 2003/0144605 A1 | 7/2003 | Burbank et al. |
| 2003/0187324 A1 | 10/2003 | Gatto |
| 2004/0044343 A1 | 3/2004 | Brommersma et al. |
| 2005/0080412 A1 | 4/2005 | Ouchi |
| 2006/0030844 A1 | 2/2006 | Knight et al. |
| 2006/0069303 A1 | 3/2006 | Couvillon |
| 2007/0093812 A1 | 4/2007 | Hayashida et al. |
| 2009/0043303 A1 | 2/2009 | Shimomura |
| 2009/0270859 A1* | 10/2009 | Hirvi ............ A61B 18/14 514/769 |
| 2012/0095458 A1 | 4/2012 | Cybulski et al. |
| 2012/0197245 A1* | 8/2012 | Burnett ............ A61B 17/12022 606/21 |
| 2013/0218243 A1 | 8/2013 | Schomacker et al. |
| 2013/0226165 A1 | 8/2013 | Manwaring et al. |
| 2014/0171824 A1 | 6/2014 | Hugle et al. |
| 2014/0236143 A1* | 8/2014 | Ward ............ A61B 18/1442 606/39 |
| 2014/0379055 A1 | 12/2014 | Schomacker et al. |
| 2015/0005799 A1 | 1/2015 | Lindquist et al. |
| 2015/0011993 A1 | 1/2015 | Horlle |
| 2015/0327753 A1 | 11/2015 | Amirana et al. |
| 2015/0351826 A1 | 12/2015 | Kroeber et al. |
| 2016/0038028 A1 | 2/2016 | Buelna et al. |
| 2016/0120599 A1 | 5/2016 | Amirana et al. |
| 2016/0192983 A1 | 7/2016 | Klink et al. |
| 2017/0014202 A1 | 1/2017 | Ransbury et al. |
| 2017/0071664 A1 | 3/2017 | Lim |
| 2019/0038341 A1 | 2/2019 | Brockmann et al. |
| 2020/0121791 A1* | 4/2020 | Zamadar ............ A61P 35/00 |

FOREIGN PATENT DOCUMENTS

| | | |
|---|---|---|
| DE | 102013001156 A1 | 7/2014 |
| DE | 102017117749 A1 | 2/2019 |
| EP | 1 221 903 B1 | 6/2006 |
| EP | 1 974 683 A1 | 10/2008 |
| EP | 3 437 581 A1 | 2/2019 |
| WO | 2017/161331 A1 | 9/2017 |

OTHER PUBLICATIONS

Apr. 8, 2022 Office Action Issued in U.S. Appl. No. 16/775,496.
May 12, 2022 Office Action issued in U.S. Appl. No. 16/811,675.
Sep. 17, 2021 Office Action Issued In U.S. Appl. No. 16/775,496.
U.S. Appl. No. 16/775,496, filed Jan. 29, 2020 in the name of Christoph Knopf.
U.S. Appl. No. 16/811,675, filed Mar. 6, 2020 in the name of Christian Brockmann et al.
U.S. Appl. No. 16/775,723, filed Jan. 29, 2020 in the name of Christian Brockmann et al.
Gerhard Lanzer. "Grundzüge Des Eisenstoffwechsels [Fundamentals of Iron Metabolism]". Klinik, 2010, vol. 6, pp. 43-46.
Jun. 24, 2022 Office Action issued in U.S. Appl. No. 16/775,723.
Dec. 1, 2022 Office Action issued in U.S. Appl. No. 16/775,723.

* cited by examiner

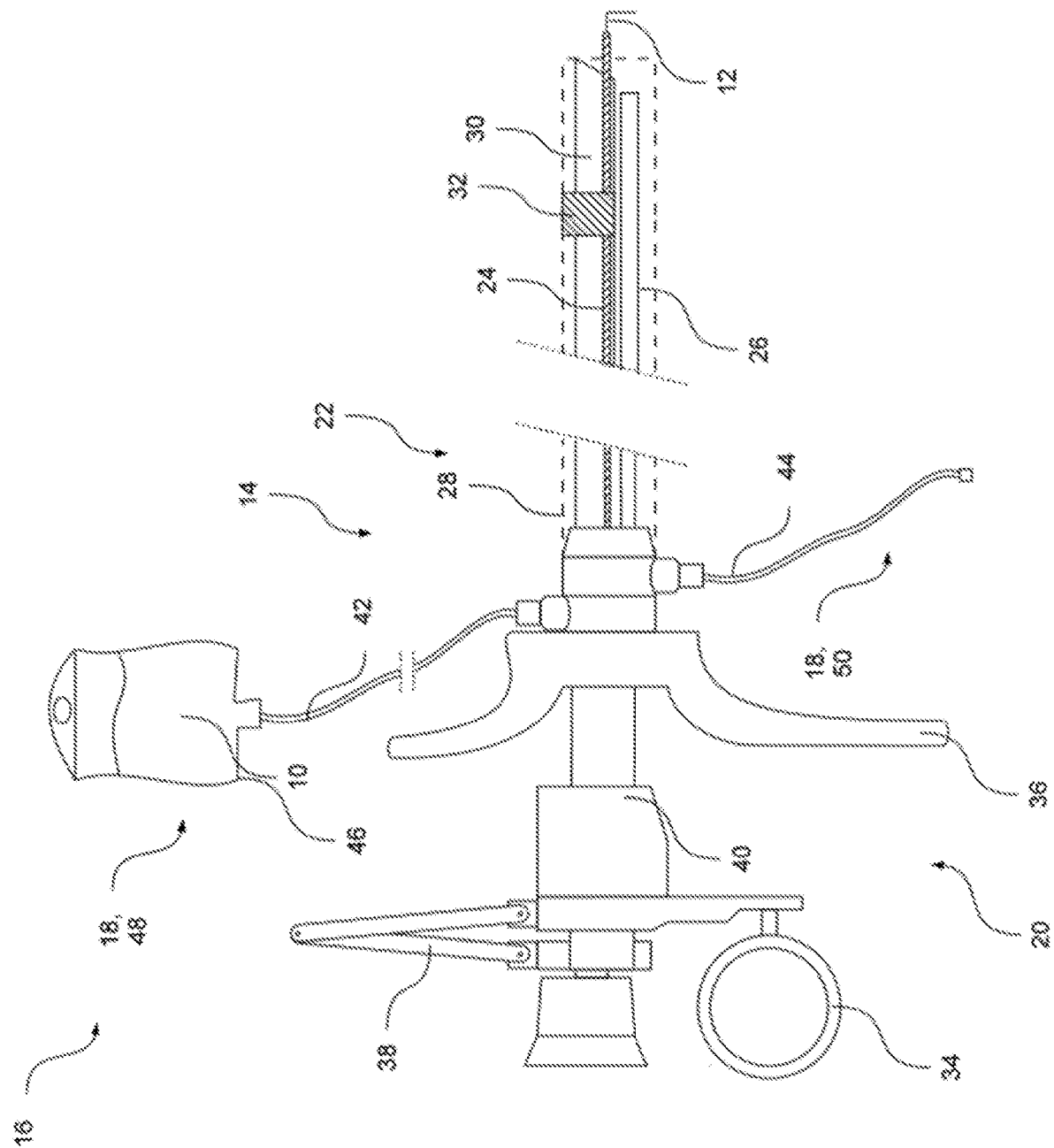

IRRIGATION FLUID FOR RESECTION

BACKGROUND

The invention relates to an irrigation fluid for use in bipolar resectoscopic surgery of the type mentioned in the preamble of claim 1 and to resectoscopy systems in which the irrigation fluid can be used.

Resectoscopy systems and irrigation fluids of this generic type are used, for example, in urology for surgical work in the bladder and in the urethra. They are usually used for resection and vaporization of tissue, for example tissue in the lower urinary tract. For this purpose, the resectoscopes used in the resectoscopy systems comprise a longitudinally displaceable electrosurgical electrode instrument which, after insertion of the resectoscope, can be pushed with its distal working end out of the distal end of the shaft tube of the resectoscope. In addition, resectoscopes for observing the site of intervention and monitoring the intervention generally contain an optical system which comprises an objective at the distal end and is connected to an eyepiece for direct observation or to an electronic monitoring unit at the proximal end, as well as a lighting element, usually in the form of an optical fiber bundle that spans the shaft of the resectoscope.

In order to flush away any local bleeding that occurs during the procedure and to protect the tissue from heat damage caused by the high-frequency electrosurgical application, the resectoscopes are equipped with an irrigation device that continuously irrigates the tissue lying in front of the distal end of the shaft. In conventional irrigation devices, irrigation fluid—e.g. physiological saline solution—is continuously passed through an inner shaft that emerges at the distal end of the resectoscope. The return flow of the irrigation fluid usually occurs through a gap between the inner and outer shaft. The outer shaft has numerous irrigation holes for receiving the fluid.

The electrode instrument that is passed through the resectoscope shaft can comprise an electrosurgical electrode in the form of a loop or PlasmaButton at its distal working end. Examples of such instruments include the OES PRO resectoscopes (Olympus). The electrode instruments can be embodied as bipolar or monopolar instruments, although bipolar instruments can have substantial safety advantages over monopolar instruments.

At present, bipolar electrodes are usually made of 1.4301 or 1.4542 stainless steel. During an operation, a glow discharge or a plasma is generated at the electrode in which hydroxyl radicals (OH•) are generated, which contribute significantly to tissue separation or tissue coagulation. Due to their reactivity, these primarily formed hydroxyl radicals have only a small effective radius. However, they react in the gas phase to form hydrogen peroxide ($H_2O_2$), which is less reactive and therefore has a larger effective radius. Using the metal ions that are dissolved out of the electrode—such as iron ions ($Fe^{3+}$), for example—the hydrogen peroxide can then be broken down again by a "Fenton-like reaction": $Fe^{2+}+H_2O_2 \rightarrow Fe^{3+}+OH•+OH^-$. The hydroxyl radicals that are generated again in this way can again contribute to tissue separation or tissue coagulation.

However, the effectiveness of the hydroxyl radical generation described above is adversely affected by the fact that the hydroxyl ions ($OH^-$) bind free metal ions, e.g., iron ions ($Fe^{3+}$): $Fe^{3+}+OH^- \leftrightarrow Fe(OH)^{2+}$. The metal ions bound in this way can therefore not contribute to the splitting of further hydrogen peroxide, so the coagulating or separating action of the electrode on the tissue is limited.

It is therefore the object of the present invention to provide an optimized resectoscope in which the coagulating and separating effect of the electrode on surrounding tissue is enhanced.

DESCRIPTION

This object is achieved by an irrigation fluid for use in bipolar resectoscopic surgery with the features of claim 1 and by a resectoscopy system with the features of claim 8.

The invention thus relates in particular to an electrically conductive irrigation fluid for use in bipolar resectoscopic surgery, the irrigation fluid being brought into contact with the electrode of a resectoscope and tissue being coagulated and/or resected by means of the electrode surrounded by the irrigation fluid, characterized in that the irrigation fluid comprises metal ions.

Through the addition of metal ions to the irrigation fluid, the concentration of Fenton reactants for hydrogen peroxide is increased at the site of intervention, so that by splitting the hydrogen peroxide into hydroxyl radicals and hydroxyl ions according to the following reaction, the concentration of reactive hydroxyl radicals at the site of intervention is increased: $Fe^{2+}+H_2O_2 \rightarrow Fe^{3+}+OH•+OH^-$ (using the example of iron ions). The reaction proceeds analogously with other reducible metal ions. The coagulating or separating effect of the electrode on the tissue can thus be substantially increased by means of the metal ion-containing irrigation solution compared to irrigation solutions lacking metal ions.

The metal ions contained in the irrigation fluid can be selected from the group consisting of ions of the metals of the 4th period of the periodic table (Sc, Ti, V, Cr, Mn, Fe, Co, Ni, Cu, Zn) and ions of the metals of subgroup VI of the periodic table (Cr, Mo, W, Sg) and mixtures thereof. The metal ions are especially preferably iron ions and/or copper ions. Iron ions, in particular, constitute a preferred variant according to the invention, since they are an endogenous substance and therefore have high biocompatibility. Iron can make up about 45 mg/kg body weight in humans, for example.

The ions of these metals are characterized in that they can react with the reaction partner hydrogen peroxide in a Fenton-like reaction to form a reduced metal ion, a hydroxyl anion, and a hydroxyl radical. In other words, the metal ions used according to the invention can be reduced by hydrogen peroxide in a Fenton-like reaction in which hydrogen peroxide is split into hydroxyl radical and hydroxyl anion. The expression "Fenton-like reaction" refers herein to an oxidation of hydrogen peroxide catalyzed by iron salts. In particular, the iron ions according to the invention can react with hydrogen peroxide to form a reduced iron ion, hydroxyl radical, and hydroxyl anion.

The metal ions can be added to the irrigation fluid in the form of various metal salts and/or metal oxides. Accordingly, in addition to the metal ions, the irrigation solution also comprises the corresponding anion of the metal salt or metal oxide, for example a sulfate anion, gluconate anion, and/or fumarate anion. The metal salts or metal oxides can be added in the form of a solution, suspension, and/or solid.

Suitable metal salts can be selected, for example, from the group consisting of metal gluconates, metal sulfates, and/or metal fumarates. The metal salt is preferably an iron salt. Suitable metal oxides can be selected, for example, from the group consisting of iron (III) oxide ($Fe_2O_3$), iron (II) oxide (FeO), copper (II) oxide (CuO), and other metal oxides.

In order to minimize the risk of side effects, the metal salts or metal oxides are biocompatible, i.e., compatible for the patient in terms of type and concentration. Iron oxides, in particular, have a high level of biocompatibility and are administered in tablet form, for example, in states of iron deficiency (cf. Lanzer G., *Grundzüge des Eisenstoffwechsels* [Fundamentals of Iron Metabolism], 2010, Klinik, 6, 43-46). Metal salts, particularly iron salts such as iron (II) gluconate and iron (II) fumarate, also have a high level of biocompatibility and are approved as food supplements, for example.

In addition, the irrigation fluid can comprise other conventional components. As will readily be understood, the irrigation fluid is an aqueous irrigation fluid. The irrigation fluid will therefore contain 60% by weight or more, preferably 70% by weight or more, more preferably 80% by weight or more, of water.

Since the irrigation solution according to the invention is intended to be suitable particularly for use in bipolar resection systems, it is conductive since the current inflow and outflow in bipolar systems runs via the active and return electrodes that are integrated into the resectoscope and not through the patient's body. The flow of current at the resection electrode creates a plasma that enables targeted and efficient incisions and coagulation of the tissue. One example of a suitable conductive irrigation solution is a saline solution comprising metal ions. The saline solution is preferably a physiological saline solution (0.9% by weight sodium chloride) or a substantially physiological saline solution. The use of irrigation solutions with a physiological salt concentration has the additional advantage that TUR (transurethral resection) syndrome is avoided. In individual cases, TUR syndrome can be caused by volume loading and electrolyte displacement during electrosurgical interventions. In some embodiments, the irrigation fluid can therefore contain 0.7% by weight or more of sodium chloride, preferably 0.8% by weight or more, more preferably 0.9% by weight or more, for example about 0.9% by weight. In other words, the irrigation fluid can contain from 0.7% by weight to 1.1% by weight, preferably from 0.8% by weight to 1.0% by weight of sodium chloride, for example. The terms "irrigation fluid" and "irrigation solution" are used synonymously herein.

Alternatively, the irrigation fluid can be a Ringer's solution that comprises metal ions. Suitable Ringer solutions that can form the basis for the irrigation solution according to the invention are known to those skilled in the art. In addition to sodium ions and chloride ions, Ringer's solutions also comprise potassium, calcium, and/or magnesium ions.

In addition, the irrigation fluid can also contain sugar alcohols such as sorbitol and mannitol. The pH of the irrigation fluid is usually between 4.5 and 7.0.

The irrigation fluid is preferably sterile in order to rule out infections during an operation.

The irrigation fluid according to the invention is used in bipolar resectoscopic surgery, preferably endoscopy. The corresponding surgical intervention can be an intervention on a human patient. During the procedure, tissue is resected and/or coagulated using an electrode. This enables tissue to be removed, for example. The resectoscopic intervention can be used for the removal of tumor tissue or for the obliteration of vessels, for example. Resectoscopic surgery can include transurethral or transcervical resection (TUR or TCR), for example.

The surgical intervention comprises a step in which the irrigation fluid is passed through a resectoscope to an electrode that is arranged in the distal end region of the resectoscope. In the currently customary manner, the irrigation fluid is conducted to the electrode at a pressure that is sufficient to also carry the irrigation fluid into the body opening located distally in front of the shaft, so that the irrigation fluid flows around the tissue lying in front of the resectoscope and the electrode.

Through the introduction of the irrigation fluid through the irrigation tube into the interior of the body during a medical intervention, it is ensured that the medical staff has a clear view of the area to be treated via the optics during the treatment. For example, tissue that is released during resectoscopy can be washed away by the irrigation fluid. Furthermore, the irrigation fluid serves to remove cloudiness caused by blood, for example, from the field of view of the optics.

Preferably, the irrigation fluid and impurities mixed therewith, such as blood and other body fluids as well as tissue fragments, for example, are then also passed out of the body again through the resectoscope. However, it is also conceivable to drain the fluid through another instrument and/or through a body opening.

In a second aspect, the invention relates to a resectoscopy system comprising a resectoscope and an irrigation system that is connected to the resectoscope, wherein the resectoscope having a handle and a tubular shaft, and the shaft comprising an electrode instrument that is arranged so as to be longitudinally displaceable and has in its distal end region an electrode to which high-frequency current can be applied, characterized in that the irrigation system comprises an irrigation fluid according to the invention, which can be conducted through the shaft of the resectoscope to the electrode.

In the standard embodiment, the resectoscope thus has a tubular shaft. In addition to this shaft part, the resectoscope for holding and operating comprises a handle, which usually consists of two handle parts.

The tubular shaft has an elongate cladding tube. An inner tube, rod-shaped optics, and an electrode instrument (electrosurgical passage instrument) are arranged in the interior of the cladding tube. Optics and electrode instrument can be arranged within the inner tube. In this arrangement, the inner tube can be used as an irrigation tube, i.e., as a tube through which the irrigation fluid can be passed through the shaft in the distal direction. Contaminated irrigation fluid can flow back through the gap between the cladding tube and the inner tube in the proximal direction. Alternatively, the irrigation fluid can be passed through a separate irrigation tube. In that case, the electrode instrument, the optics, and/or an inner tube serving the function of a working channel for the passage instruments would be arranged radially next to the irrigation tube. In this arrangement, the return flow of the irrigation fluid could take place in the space in the cladding tube that is located outside of the irrigation tube, for example.

As mentioned, the shaft comprises an electrode instrument that is arranged so as to be longitudinally displaceable and has an electrode to which high-frequency current can be applied in its distal end region. Suitable electrode instruments are known to those skilled in the art. The electrode instrument generally has an elongate instrument shaft and at least one electrode arranged on the distal end region. In addition to this active electrode, the electrode instrument preferably also has a neutral electrode. This enables bipolar electrosurgical interventions to be performed. The electrode (active electrode) can be embodied, for example, as a vaporization button (e.g., PlasmaButton), cutting loop, or another electrosurgical cutting tool, a cutting loop being preferred. The electrode instrument is preferably a bipolar instrument.

According to the invention, the electrode comprises or consists of an electrically conductive, preferably metallic material. The material is preferably selected from the group consisting of: Metals of the 4th period of the periodic table (Sc, Ti, V, Cr, Mn, Fe, Co, Ni, Cu, Zn) and metals of subgroup VI of the periodic table (Cr, Mo, W, Sg), as well as alloys that comprise the above materials. Preferably, the material is a steel, more preferably a stainless steel. Stainless steels are steels whose sulfur and phosphorus content is less than 0.025%. The steel used is suitable for use in surgical instruments. Steels suitable for this use are known to those skilled in the art and described in ISO 7153-1, for example. In the context of the invention, the electrode thus comprises or consists in particular of a steel described in ISO 7153-1. The electrode preferably comprises iron. For example, the electrode can comprise a steel that is selected from the group consisting of: 1.4301 (according to DIN: X5CrNi18-10) and 1.4542 (according to DIN: X5CrNiCuNb17 44), or it can be composed of one of these steels.

The electrode instrument can have two fork tubes. Such a construction is known for many electrode instruments, particularly bipolar instruments with a cutting loop at the distal end, for example. These fork tubes usually run relatively close to one another in the proximal and middle shaft region of the electrode instrument and only diverge in the distal end region of the electrode instrument, so that the distal ends of the fork tubes can hold an electrode between them, for example in the form of a loop electrode or a PlasmaButton.

The electrode instrument is longitudinally displaceable within the shaft of the resectoscope, meaning that it can be moved distally and proximally in the axial direction. For connection to the resectoscope, the electrode instrument has the abovementioned elongate shaft, which can be fastened at its proximal end to a slide that is encompassed by the resectoscope in order to produce a movement-coupled connection. The slide typically slides on a tube and is spring biased by a spring unit into a rest position. The electrode at the distal end can thus be moved toward or away from tissue to be resected without the need to move the entire resectoscope. Moreover, the longitudinal displaceability of the electrode instrument makes it possible to clamp tissue between the electrode and the distal end of the inner tube and remove it from the site of intervention. The distal end of the inner tube and the electrode can thus be moved toward and away from one another by virtue of the longitudinal displaceability of the electrode instrument.

The electrode instrument that is used according to the invention can have one or more holding elements for radial support. This prevents undesired lateral displacement of the electrode during an operation. At the same time, the electrode instrument can be displaced in the axial direction. The electrode, which is arranged at the distal end of the electrode instrument, can thus be used to remove tissue. The axial displaceability of the electrode instrument is not affected by the holding elements. It is conceivable to stabilize individual additional components that pass through the shaft part of the resectoscope against one another, particularly counter to a displacement in the radial direction.

The optics of the present resectoscope that are arranged in the shaft are rod-shaped optics which, in turn, have a shaft region that runs through the resectoscope shaft. The optics enable the user to visually monitor the site of intervention and the electrosurgical intervention being performed. The optics can comprise a lens-based optics system or fiber optics. In their proximal end region, the optics include an eyepiece or a connection to a camera head. At their distal end, the optics are usually protected by a protective glass that can also act as a filter. The optics can be optics having an inclined viewing angle in order to ensure an especially good view of the site of intervention.

The resectoscope system also has an irrigation system that is connected to the resectoscope. The irrigation system comprises an irrigation fluid according to the invention that can be conducted through the shaft to the electrode, for example through an irrigation tube or an inner tube. As a rule, the irrigation fluid is passed through the shaft at a pressure that is sufficient to ensure that the irrigation fluid flows around the electrode and the site of intervention.

The irrigation system comprises an irrigation fluid supply means. This contains one or more containers or reservoirs with irrigation fluid. The container can be a bag or canister, for example. The container is preferably a bag in the manner of an infusion bag. The irrigation fluid supply means can further comprise a pump that is suitable for pumping the irrigation fluid into the shaft. Alternatively, the irrigation fluid can flow into the shaft, driven by hydrostatic pressure. In this embodiment, the container would have to be arranged above the resectoscope in the resectoscopy system according to the invention.

The container is connected to the irrigation tube of the resectoscope via tube or hose connections, so that the irrigation fluid can flow from the container into the irrigation tube.

The irrigation system can also be an irrigation fluid discharging means. This is connected to a return channel of the resectoscope in such a way that contaminated irrigation fluid can flow through it out of the resectoscope. As described elsewhere herein, the return channel can be formed, for example, by the space between the cladding tube and the inner tube. A drain hose or drain tube of the irrigation fluid discharge means can be arranged at the proximal end of the return channel. While active pumping-out by means of a pump is conceivable, the discharge can also be driven by hydrostatic pressure. In this case, at least portions of the irrigation fluid discharge means should be arranged below the resectoscope.

In another aspect, the invention relates to an endoscopic surgical method which characterized in that it comprises steps in which: (a) an irrigation fluid according to the invention is provided; (b) an electrode that is arranged in the distal end region of a resectoscope is introduced into the body of a patient in need of a resectoscopic endoscopic intervention; (c) the irrigation fluid is delivered to the electrode; and (d) tissue is coagulated and/or resected by means of the electrode that is surrounded by the irrigation fluid. The delivery in step c) can take place, for example, by means of an irrigation system according to the invention.

BRIEF DESCRIPTION OF THE FIGURES

One exemplary embodiment of the invention is illustrated schematically in the drawing, in which:

FIG. 1 shows a schematic, sectional side view of an electrosurgical system according to the invention, which has an irrigation system.

EXEMPLARY EMBODIMENTS

Additional advantages, characteristics, and features of the present invention will become clear from the following detailed description of an exemplary embodiment with reference to the attached drawing. However, the invention is not restricted to this exemplary embodiment.

FIG. 1 shows a sectional representation of a resectoscopy system 16 according to the invention, which comprises a resectoscope 14 and an irrigation system 18. The resectoscope 14 and the irrigation system 18 are functionally connected to one another, particularly in such a way that irrigation fluid 10 can be conducted from the irrigation system 18 into the resectoscope 14, particularly into the shaft 22, it being possible for the irrigation fluid 10 to exit the resectoscope 14 at the distal end of the shaft 22.

In a standard embodiment, the resectoscope 14 comprises a handle 20 and a shaft 22. The handle 20 is designed to enable the resectoscope 14 to be held in one hand and for the passage instruments running through the shaft 22 to be actuated, preferably with one hand.

The resectoscope 14 shown has a passive transporter in which the slide 40 is displaced in the distal direction against the distal, first handle part 36 through a relative movement of the handle parts 34 and 36 that are arranged proximally from the shaft 22 against a spring force that is applied by a spring bridge 38. When the slide 40 is displaced in the distal direction against the handle part 36, the electrode instrument 24 is positively guided to the distal in a manner not shown. When the handle parts 34, 36 are released, the spring force generated by the spring bridge 38 forces the slide 40 back into its resting position, the electrode instrument 24 being pulled in the proximal direction. When the slide 40 is moved back, an electrosurgical intervention with the electrode instrument 24 can be carried out without manual force on the part of the surgeon—that is, passively.

The shaft 22 of the resectoscope 14 comprises a cladding tube 28 in whose interior a plurality of elongate passage instruments extend, particularly the elongate optics 30, the electrode instrument 24, and the irrigation tube 26. In the embodiment shown in FIG. 1, no additional passage instruments are arranged in the interior of the irrigation tube 26. Instead, the electrode instrument 24 and the optics 30 are arranged next to the irrigation tube 26 in the cladding tube 28. For stability, the electrode instrument 24 is secured by a holding element 32 against radial displacement. The holding element 32 has a partially circular cross section which, in the present instrument, bears against the inner wall of the cladding tube 28 approximately along half the inner circumference of the inner wall. The cross section of the holding element 32 is thus approximately semicircular in the present case. As a result, the electrode instrument 24 can be displaced in the axial direction inside the cladding tube 28 while it is being supported radially.

At its distal end, the electrode instrument 24 has an electrode 12 which, in the present case, is embodied as a loop electrode or cutting loop. The electrode instrument 24 is embodied as a bipolar instrument and is provided with a counterelectrode (not shown). By means of the electrode 12, the medical staff is able to remove tissue from the site of the intervention during a surgical intervention.

Irrigation fluid 10 can be conducted through the irrigation tube 26 to the site of intervention in the distal direction. The return flow of the contaminated irrigation fluid takes place through the empty space that remains inside the cladding tube 28 next to the passage instruments arranged therein—that is, the space that remains next to the optics 30, irrigation tube 26, and electrode instrument 24.

The resectoscopy system 16 also has an irrigation system 18 having an irrigation fluid supply means 48 which, in the embodiment shown, comprises a fluid reservoir 46 with irrigation fluid 10 and a supply hose 42. The irrigation fluid 10 flows through the supply hose 42 into the irrigation tube 26 of the resectoscope 14. The irrigation fluid 10 comprises approximately 0.9% by weight of NaCl and iron oxide.

In the embodiment shown, the irrigation fluid 10 flows into the irrigation tube 26 as a result of the hydrostatic pressure of the fluid in the fluid reservoir 46. The speed of the irrigation fluid 10 can be adjusted by changing the height of the fluid reservoir 46 relative to the resectoscope 14. Upon reaching the site of intervention, the irrigation fluid 10 can flow off again through the space between the inner wall of the cladding tube 28 and the passage instruments arranged therein.

The irrigation system 18 further comprises an irrigation fluid discharge means 50 which, in the embodiment shown, is embodied as a drain hose 44 through which the contaminated fluid can drain.

Although the present invention has been described in detail with reference to the exemplary embodiment, it is obvious to those skilled in the art that the invention is not restricted to this exemplary embodiment, but rather that modifications can be made in such a way that individual features are omitted or other combinations of the individual features presented are realized, provided that the scope of protection of the appended claims is not exceeded. The present disclosure includes any and all combinations of the individual features presented.

LIST OF REFERENCE SYMBOLS

| | |
|---|---|
| 10 | irrigation fluid |
| 12 | electrode |
| 14 | resectoscope |
| 16 | resectoscopy system |
| 18 | irrigation system |
| 20 | handle |
| 22 | shaft |
| 24 | electrode instrument |
| 26 | irrigation tube |
| 28 | cladding tube |
| 30 | optics |
| 32 | holding element |
| 34 | handle part |
| 36 | handle part |
| 38 | spring bridge |
| 40 | slide |
| 42 | supply hose |
| 44 | drain hose |
| 46 | fluid reservoir |
| 48 | irrigation fluid supply means |
| 50 | irrigation fluid discharge means |

The invention claimed is:

1. An electrically conductive irrigation fluid for use in bipolar resectoscopic surgery, the irrigation fluid comprising:
   metal ions selected from the group consisting of ions of the metals of the 4th period of the periodic table (Sc, Ti, V, Cr, Mn, Fe, Co, Ni, Cu, Zn) and ions of the metals of subgroup VI of the periodic table (Cr, Mo, W, Sg) and mixtures thereof,
   wherein the irrigation fluid is brought into contact with the electrode of a resectoscope and tissue is coagulated and/or resected by means of the electrode surrounded by the irrigation fluid.

2. The irrigation fluid as set forth in claim 1, wherein the metal ions are iron ions and/or copper ions.

3. The irrigation fluid as set forth in claim 1, wherein the metal ions can be reduced by means of hydrogen peroxide in a Fenton-like reaction in which hydrogen peroxide is split into hydroxyl radical and hydroxyl anion.

4. The irrigation fluid as set forth in claim 1, wherein the metal ions of the irrigation fluid were supplied in the form of one or more metal oxides and/or metal salts.

5. The irrigation fluid as set forth in claim 1, further comprising 0.7% by weight or more of sodium chloride.

6. The irrigation fluid as set forth in claim 1 for use in bipolar transurethral or transcervical resection.

7. A resectoscopy system, comprising:
 a resectoscope comprising:
  a handle; and
  a tubular shaft comprising an electrode instrument that is arranged so as to be longitudinally displaceable and which has in its distal end region an electrode to which high-frequency current can be applied; and
 an irrigation system that is connected to the resectoscope, the irrigation system comprising an irrigation fluid according to claim 1, which can be conducted through the shaft of the resectoscope to the electrode.

8. The resectoscopy system as set forth in claim 7, wherein the shaft comprises an irrigation tube through which the irrigation fluid can be conducted to the electrode.

9. The resectoscopy system as set forth in claim 7, wherein the electrode comprises a material that is selected from the group consisting of:
 metals of the 4th period of the periodic table (Sc, Ti, V, Cr, Mn, Fe, Co, Ni, Cu, Zn) and metals of subgroup VI of the periodic table (Cr, Mo, W, Sg) and alloys that comprise the above materials.

10. The irrigation fluid as set forth in claim 1, wherein the irrigation fluid is an aqueous irrigation fluid.

11. The irrigation fluid as set forth in claim 1, wherein the irrigation fluid has a pH in a range of 4.5 to 7.0.

12. An electrically conductive irrigation fluid for use in bipolar resectoscopic surgery, the irrigation fluid comprising:
 metal ions selected from the group consisting of ions of the metals of the 4th period of the periodic table (Sc, Ti, V, Cr, Mn, Fe, Co, Ni, Cu, Zn) and ions of the metals of subgroup VI of the periodic table (Cr, Mo, W, Sg) and mixtures thereof,
 wherein when the irrigation fluid is brought into contact with an electrode of a resectoscope, tissue is coagulated and/or resected by means of the electrode surrounded by the irrigation fluid.

13. An endoscopic surgical method comprising:
 delivering an irrigation fluid according to claim 12 to an electrode that is arranged in a distal end region of a resectoscope while the resectoscope is introduced into the body of a patient in need of a resectoscopic endoscopic intervention; and
 generating a plasma at the electrode while the electrode is surrounded by the irrigation fluid, and coagulating and/or resecting tissue of the patient with the plasma.

* * * * *